(12) United States Patent
Chiu et al.

(10) Patent No.: US 8,173,413 B2
(45) Date of Patent: *May 8, 2012

(54) SEPARATION AND CONCENTRATION OF BIOLOGICAL CELLS AND BIOLOGICAL PARTICLES USING A ONE-DIMENSIONAL CHANNEL

(75) Inventors: Daniel T. Chiu, Seattle, WA (US); Jason S. Kuo, Seattle, WA (US)

(73) Assignee: University of Washington, Seattle, WA (US)

( * ) Notice: Subject to any disclaimer, the term of this patent is extended or adjusted under 35 U.S.C. 154(b) by 558 days.

This patent is subject to a terminal disclaimer.

(21) Appl. No.: 11/202,416

(22) Filed: Aug. 11, 2005

(65) Prior Publication Data

US 2007/0037172 A1 Feb. 15, 2007

(51) Int. Cl.
*C12M 1/00* (2006.01)
(52) U.S. Cl. .................................................. 435/283.1
(58) Field of Classification Search .............. 435/6, 4, 435/283.1, 287.1–287.3; 436/514–516, 518
See application file for complete search history.

(56) References Cited

U.S. PATENT DOCUMENTS

| | | | |
|---|---|---|---|
| 4,923,608 A | 5/1990 | Flottmann et al. | |
| 5,234,594 A | 8/1993 | Tonucci et al. | |
| 5,726,026 A | 3/1998 | Wilding et al. | |
| 5,731,211 A | 3/1998 | Ohlin | |
| 5,837,115 A | 11/1998 | Austin et al. | |
| 6,623,860 B2 * | 9/2003 | Hu et al. .................. | 428/411.1 |
| 6,720,157 B2 | 4/2004 | Indermuhle et al. | |
| 6,730,516 B2 | 5/2004 | Jedrejewski et al. | |
| 6,949,355 B2 * | 9/2005 | Yamanishi et al. ........... | 435/34 |
| 7,217,542 B2 * | 5/2007 | Tyvoll et al. ................. | 435/91.1 |
| 2002/0164825 A1 * | 11/2002 | Chen .............................. | 436/526 |
| 2005/0003411 A1 | 1/2005 | Chiu et al. | |
| 2007/0037172 A1 | 2/2007 | Chiu et al. | |
| 2007/0160503 A1 | 7/2007 | Sethu et al. | |
| 2007/0160504 A1 | 7/2007 | Parthasarathy et al. | |

FOREIGN PATENT DOCUMENTS

| | | | |
|---|---|---|---|
| WO | WO9813131 | * | 4/1998 |
| WO | WO-9813131 A1 | | 4/1998 |
| WO | WO2006079007 | * | 7/2006 |
| WO | WO 2006/104474 A2 | | 10/2006 |
| WO | WO 2006/116327 A1 | | 11/2006 |
| WO | WO 2006/127256 A2 | | 11/2006 |
| WO | WO 2007/021409 A1 | | 2/2007 |

OTHER PUBLICATIONS

"International Search Report and Written Opinion for Application No. PCT/US2006/027099, Mailed Oct. 31, 2006", 11 Pages.

Lim, D. S., et al., "Parametric investigation on the effect of channel topologies on electrophoretic separations", *Journal of Chromatrography*, 1027(1-2), Elsevier Science Publishers B.V. Amsterdam, NL, (Feb. 20, 2004), 237-244.

Kuo, Jason S. et al. "Deformability considerations in filtration of biological cells," Lab Chip, 2010, vol. 10, pp. 837-842.

* cited by examiner

*Primary Examiner* — Ann Lam
(74) *Attorney, Agent, or Firm* — Kilpatrick Townsend & Stockton LLP

(57) ABSTRACT

This document discloses, among other things, a method and system for a substrate having a bypass region for fluid flow. The substrate includes a plurality of fluid flow channels with each channel configured to concurrently allow fluid flow while precluding passage of a target particle or object.

18 Claims, 18 Drawing Sheets

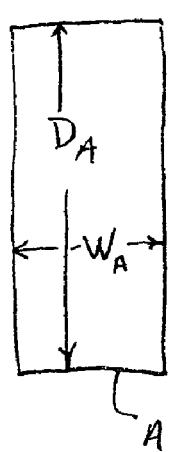
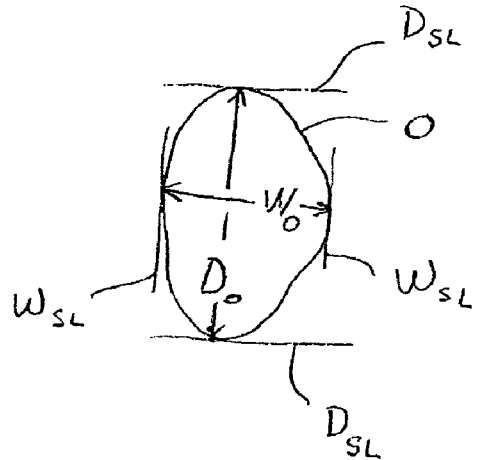
FIG. 1C  FIG. 1D
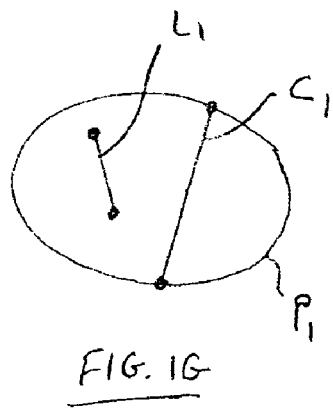
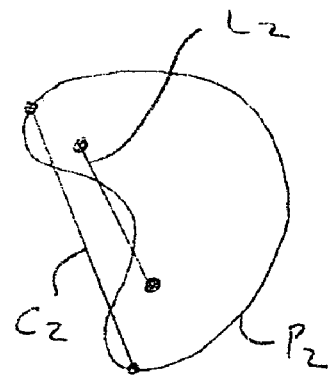
FIG. 1G  FIG. 1H
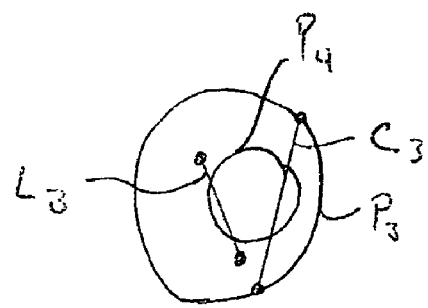
FIG. 1J

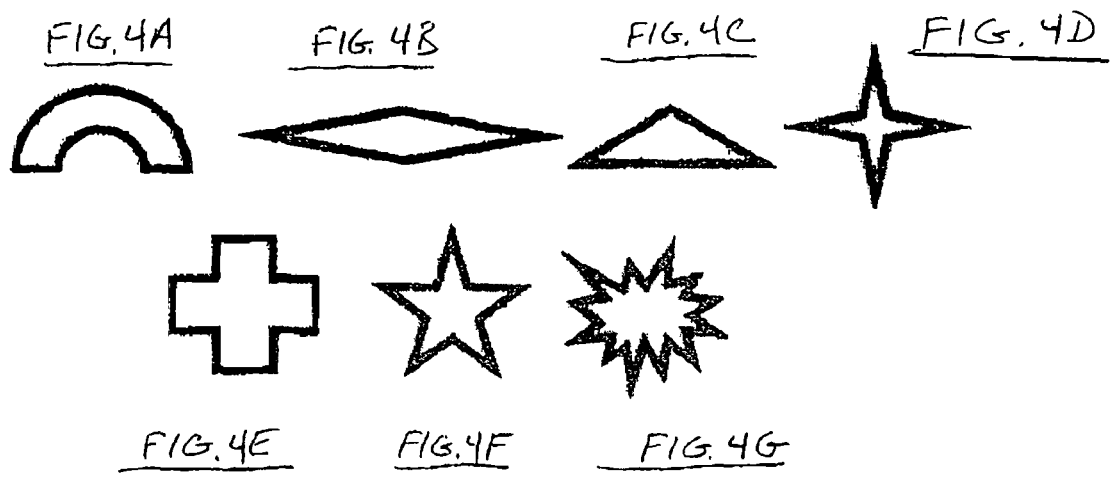

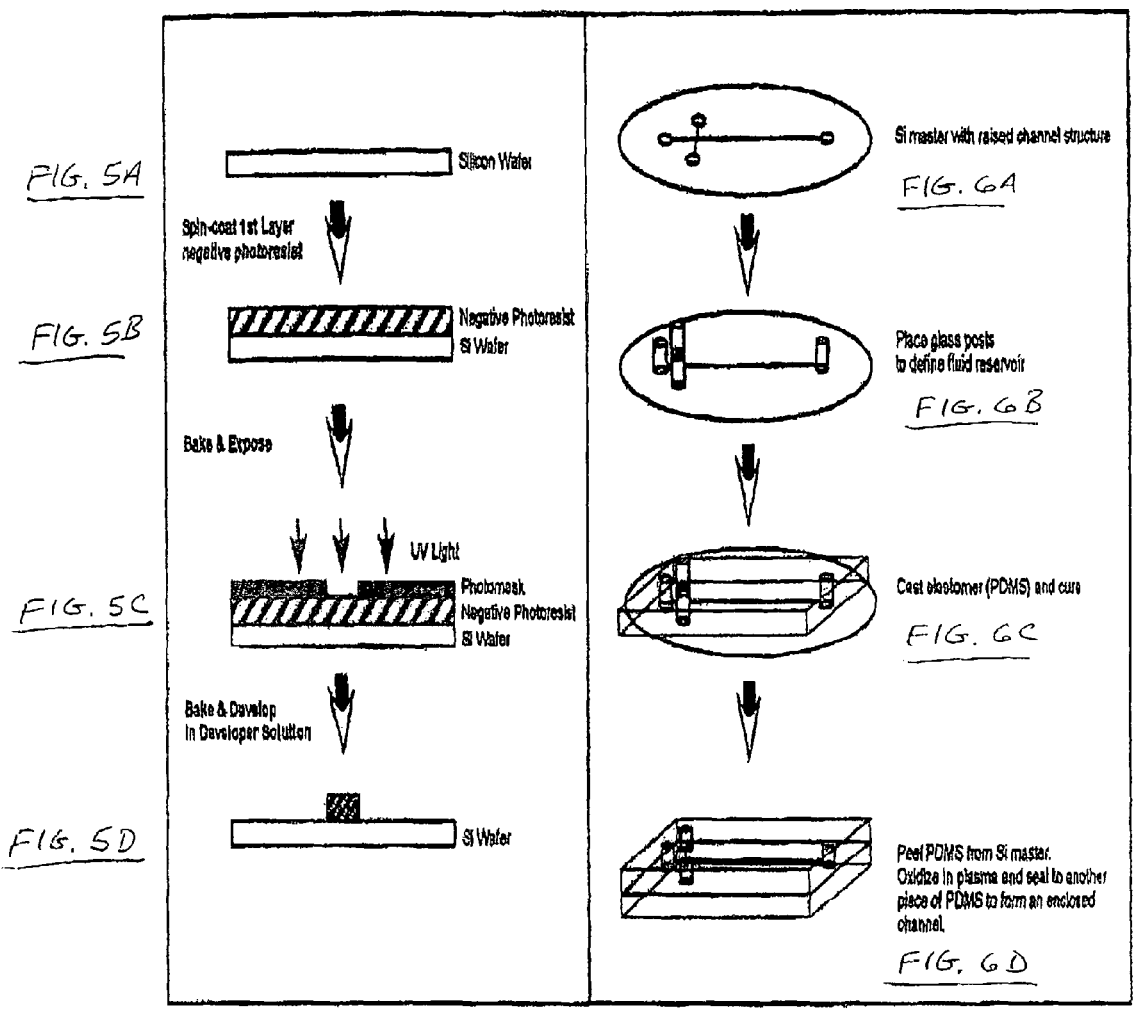

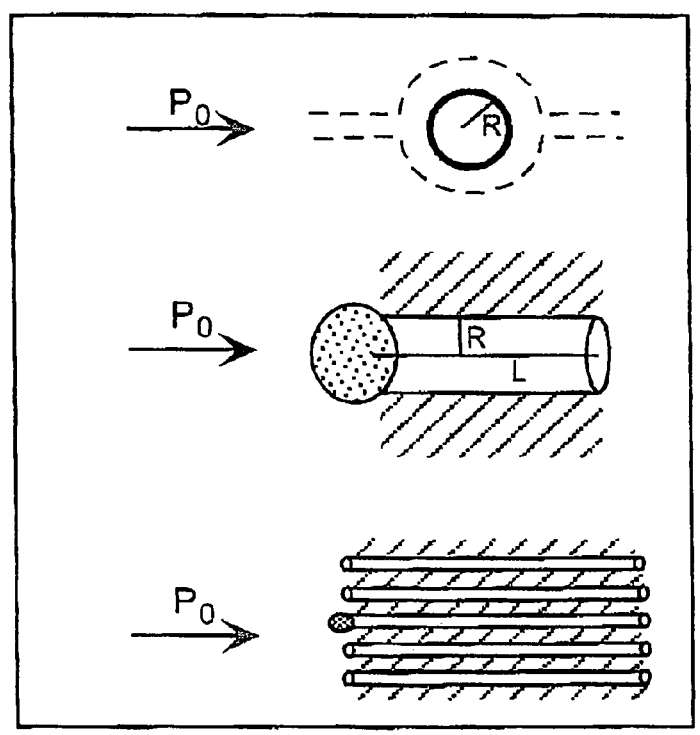

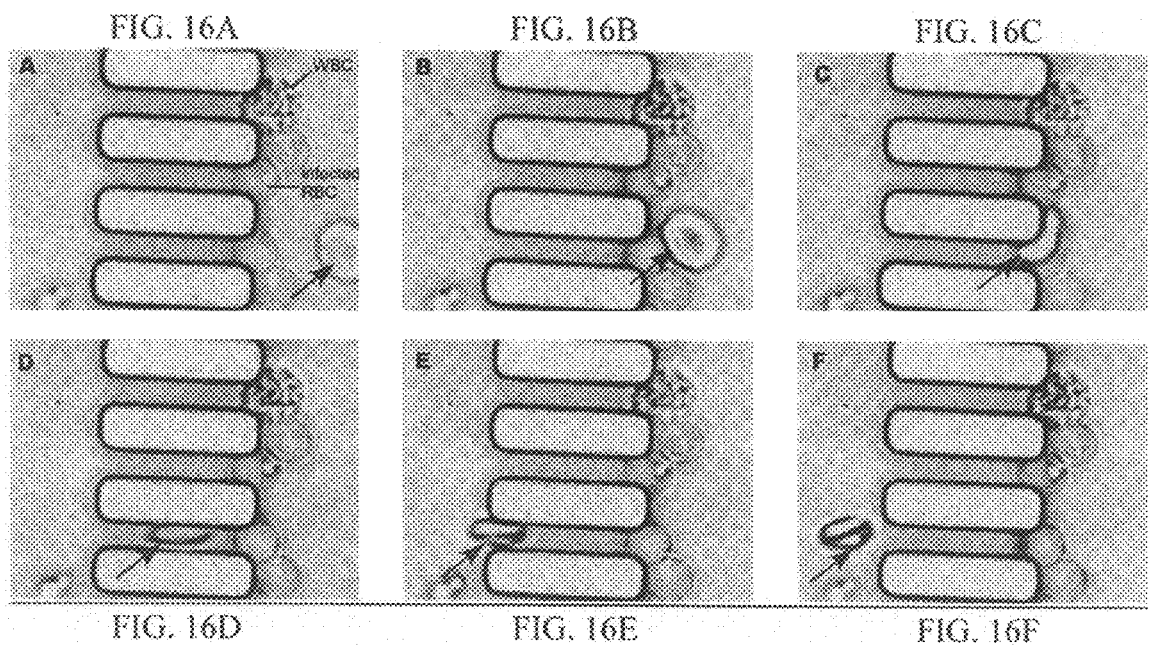

SEPARATION AND CONCENTRATION OF BIOLOGICAL CELLS AND BIOLOGICAL PARTICLES USING A ONE-DIMENSIONAL CHANNEL

GOVERNMENT FUNDING

The subject matter described herein was made with U.S. Government support under National Institute of Health (NIH) Grant Number R01 GM65293 and the Puget Sound Partners for Global Health Pilot Project (PSPGH). The United States Government has certain rights in the invention.

TECHNICAL FIELD

This document pertains generally to methods and systems for isolating, separating, and concentrating biological cells and biological particles from complex biofluid mixtures and, in particular but not by way of limitation, to methods and systems with features to reduce cell lysis or cellular membrane damage during cell and particle isolation and separation.

BACKGROUND

Body fluid is a complex mixture of different cell types and biological particles. Blood, for example, includes plasma and cells (red blood cells, white blood cells, platelets) and the cells occupy about 55% of blood. Plasma is mostly water and it transfers proteins, ions, vitamins, enzymes, hormone, and other chemicals to cells in the body. Red blood cells are about 6 to 8 μm in size and serve to provide oxygen to cells. White blood cells are about 10 to 13 μm in diameter and they defend the body from disease as a part of an immune system by fighting against foreign virus and bacteria. Platelets are the smallest cells, 1.5 to 3 μm, and they stop bleeding by forming blood clots. Fluids in addition to blood, such as saliva, tear, urine, cerebral spinal fluid as well as other body fluids in contact with various organs (e.g. lung) contain mixtures of cells and bioparticles.

The type and amount of cells and bioparticles that are present in a particular body fluid (e.g. blood) includes information about the health of the organism, and in the case of an infected individual, information about the diagnosis and prognosis of the disease. For example, anemia can be diagnosed by counting the number of red blood cells within a unit volume of blood. Similarly, elevated white blood cell count is a standard screen for signs of heightened immune response, which is often due to infection.

In diseases such as HIV, the level of CD4+ T-lymphocytes (CD4+ T-cells) in blood indicates the degree of disease progression. In fact, the CDC Public Health Service recommends monitoring the level of CD4+ T-cells every 3-6 months in all HIV-infected persons as a way to initiate appropriate treatment strategies. Another example is malaria diagnosis, in which the number of parasitized erythrocytes among normal erythrocytes and leucocytes is counted. Yet another example is in cancer diagnosis and prognosis—tumor cells can exfoliate from solid tumors and transport throughout the body via the blood stream or other body fluids (e.g. lung cancer cells may exfoliate into the fluid in contact with the lung and prostate cancer cells into urine). These circulating tumor cells are present in extremely low concentrations, and their isolation and detection among the other cells present in the fluid is required for diagnosis and prognosis.

SUMMARY

In one example, the present subject matter includes a micro-fabricated or nano-fabricated device having channels configured for separating and excluding.

The present subject matter can be used to separate and enrich cells of interest (e.g. cancer cells, lymphocytes, malaria-infected red blood cell) from other cells that may be present in a body fluid. Some biological cells have cellular membranes that are not rigid and are thus highly sensitive to local pressure changes that are often present in the process of physical exclusion and separation. For example, in isolating cells by mechanical exclusion, exposure of the cells to a high-pressure environment can cause cell lysis. To overcome these challenges in the separation and concentration of biological cells and particles, the present subject matter includes devices and methods for separating and concentrating biological cells and particles, while reducing the incidence of cell lysis during the separation, concentration, filtration or isolation procedure.

The present subject matter includes channels having a particular cross-sectional shape for separating subpopulation of cells from biofluids or immiscible objects from a fluid. The cross-sectional shape of the channels, as employed in embodiments of the present subject matter, reduce the hydrodynamic pressure experienced by the cells during the separation, isolation and concentration processes and therefore reduce the likelihood of cellular damage.

The present subject matter can be used as diagnostic aids for leucocyte counting, parasite quantification in malaria, CD4+ T-lymphocyte cell counting in HIV-infection progress monitoring, in trapping rare circulating tumor cells (CTCs) in cancer monitoring, as well as trapping circulating fetal cells in prenatal diagnosis of genetic disorders.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1C illustrates an aperture of rectangular configuration.

FIG. 1D illustrates an arbitrary object.

FIGS. 1G, 1H, and 1J illustrate apertures.

FIGS. 4A-4G illustrate various aperture cross sections.

FIGS. 5A-5D illustrate a sequence for fabricating an exemplary device.

FIGS. 6A-6D illustrate a sequence for fabricating an exemplary device.

FIGS. 11A-11C illustrate various scenarios that a biological cell or particle can experience pressure forces.

FIGS. 16A-16F illustrate trapping of malaria-infected red blood cells (RBC) and white blood cells (WBC).

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Biological cells are often sensitive to local pressure change because cellular membranes are not rigid. In filtering or isolating cells by mechanical exclusion, exposure of the cells to a high pressure environment can cause lysing. Lysis refers to the disintegration, rupturing or destruction of a cell or bacteria. With a cell, such a breakdown is caused by damage to the plasma (outer) membrane and subsequent loss of cell contents (cytoplasm, organelles or nucleus) resulting from physical insult to the cell. The present subject matter reduces the incidence of lysis in separation, concentration, filtration or isolation.

The present subject matter relates to a micro-fabricated and nano-fabricated device and method useful for separating, concentrating and isolating microscopic or nanoscopic objects such as biological cells, macromolecules, colloidal particles, particulates, or micro-beads and nano-beads using an array of one-dimensional channels. The device may be used to isolate, purify, and concentrate a subpopulation of biological cells to facilitate clinical diagnosis of diseases such as malaria, AIDS and cancer.

As used herein, a fluid can include a liquid or a gas and an object or target particle can include a cell, a bacteria, a virus, a biological nano-particulate, a biological micro-particulate or other object. The target particle can include an organic or inorganic object.

Figure 1A:
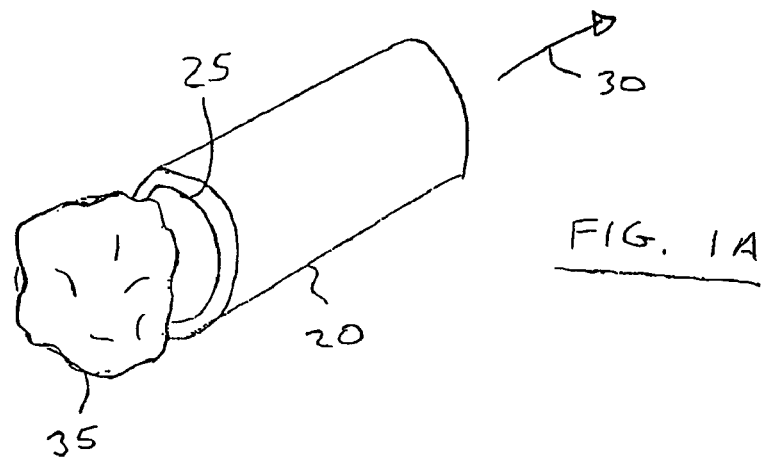
FIG. 1A illustrates a zero-dimensional channel with a target particle.
Figure 1B:
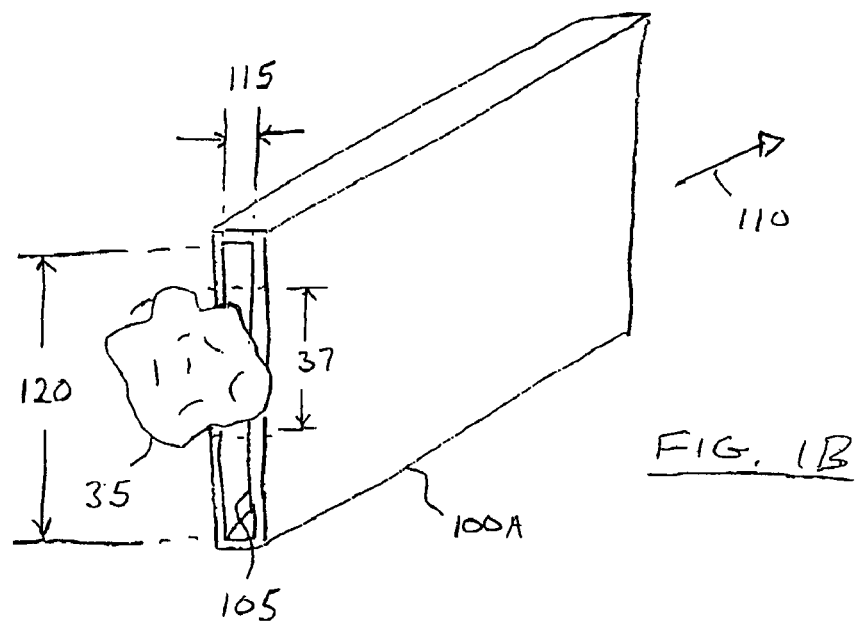
FIG. 1B illustrates a one-dimensional channel with a target particle.

FIGS. 1A and 1B illustrate sample geometry for mechanically excluding a cell, particulate or other immiscible objects from the immersed carrier fluid. FIG. 1A illustrates a geometric configuration where circular channel 20 is used to exclude target particle 35. In this figure, target particle 35 is disposed near lumen 25 of channel 20 and arrow 30 denotes the fluid flow direction, which is a manifestation of a pressure differential between an input side and an output side of channel 20. Since the approximate outside diameter of target particle 35 is larger than the diameter of lumen 25, with the fluid flow traversing along the channel as shown by arrow 30, lumen 25 is occluded. When occluded, fluid flow in channel 20 ceases. With continued application of the pressure differential, such as for example, in an attempt to re-establish the flow, under some circumstances, target particle 35 will distort and possibly rupture.

Channel 20 is shown to have a circular cross section and is sometimes referred to as a zero-dimensional channel. A zero-dimensional channel has a pore with a diameter (or mean diameter in the case of filters based on cross-linked or highly branched matrices) smaller than the dimensions of the object intended to block, and thus mechanically prevents an object of diameter larger than that of the channel from traversing through the channel. The entrance of the channel becomes enriched with the excluded object and the fluid passing through the channel, which is sometimes referred to as the filtrate, becomes devoid of the excluded object, thus accomplishing isolation of the object, separation of the object from the filtrate, and concentration of the object near the entrance.

FIG. 1B illustrates channel 100A having a cross-sectional geometry according to the present subject matter which also provides mechanical exclusion of target particle 35 in fluid flow direction indicated by arrow 110. In the figure, channel 100A is sometimes referred to as a one-dimensional channel. A one-dimensional channel has an aperture cross sectional geometry such that a chord of length larger than the diameter of the object to be excluded can be drawn. In addition, the cross-sectional geometry also has a chord of length less than the width of the object. For example, in the figure, channel 100A has a rectangular exterior configuration and uniform wall thickness, thus forming rectangular aperture 105. Aperture 105 has a diameter, as denoted by dimension 120, and a width, as denoted by dimension 115. Target particle 35 has an average diameter denoted by dimension 37. As illustrated, width dimension 115 is smaller than dimension 37, and thus, particle 35 is precluded from passing through channel 100A. With target particle 35 lodged in the constriction formed by the dimensional difference between width dimension 115 and diameter dimension 37, fluid flow in channel 100A is allowed to continue since diameter dimension 120 is larger than diameter dimension 37. Fluid bypasses the constriction and passes around target particle 35 in the presence of continued application of a pressure differential. Pressure build-up on the surface of target particle 35 remains relatively low since fluid is allowed to bypass.

FIGS. 1C and 1D illustrate channel geometries in accordance with the present subject matter. FIG. 1C illustrates aperture A having cross sectional geometry in the form of a rectangle. Dimension $D_A$ represents a diameter of the aperture and dimension $W_A$ a width of the aperture. The width represents a minimum distance that can be drawn between two parallel supporting lines. The supporting lines are tangents of the perimeter. The diameter represents a maximum distance that can that can be drawn between two parallel supporting lines. In the case of the rectangular shaped aperture, the supporting lines are co-linear with the sides of the aperture.

FIG. 1D illustrates arbitrary object O having width denoted by $W_O$ and diameter denoted by $D_O$ for a particular cross section, defined as the minimum and the maximum distances, respectively, that can be drawn between two parallel support lines. In the case of object O, the diameter supporting lines are denoted $D_{SL}$ and the width supporting lines are $W_{SL}$.

Aperture A will exclude object O when, for a particular cross section, $W_O$ is greater than $W_A$. Aperture A has cross sectional geometry that can be described as convex. A shape is convex if it wholly contains the straight line that joins any two points inside the shape. FIG. 1G illustrates convex shape $P_1$ in which line segment $L_1$ denotes a representative line segment having points that lie entirely within the perimeter of shape $P_1$.

According to the present subject matter, a one-dimensional channel (having an aperture with convex cross sectional geometry) can be described as a channel wherein the aperture width is smaller than the width of the object to be excluded and the aperture diameter of the channel is larger than the diameter of the object as well as larger than the width of the aperture. A channel of circular aperture, wherein the aperture diameter is equal to the aperture width, is not considered as a one-dimensional channel.

More generally, the present subject matter includes a channel having an aperture cross sectional geometry such that a chord of length larger than the diameter of the object to be excluded can be drawn. A chord is a straight line formed between two points on the perimeter of the shape. A chord may cross the perimeter. In other words, a chord may pass through the region enclosed by the perimeter as well as the region outside of the perimeter. FIGS. 1G, 1H and 1J illustrate exemplary shapes having chords $C_1$ (perimeter $P_1$), $C_2$ (perimeter $P_2$) and $C_3$ (perimeters $P_3$ and $P_4$), respectively.

The shapes illustrated in FIGS. 1H and 1J can be described as non-convex or concave. A shape is concave, or non-convex, if it has the property that the line segment connecting any two interior points is not totally contained in the shape. The shapes illustrated in FIGS. 1H and 1J, for example, are concave since line segments $L_2$ and $L_3$, respectively, can be drawn such that they cross the boundaries or perimeters of the shape.

Figures 1E, 1F:
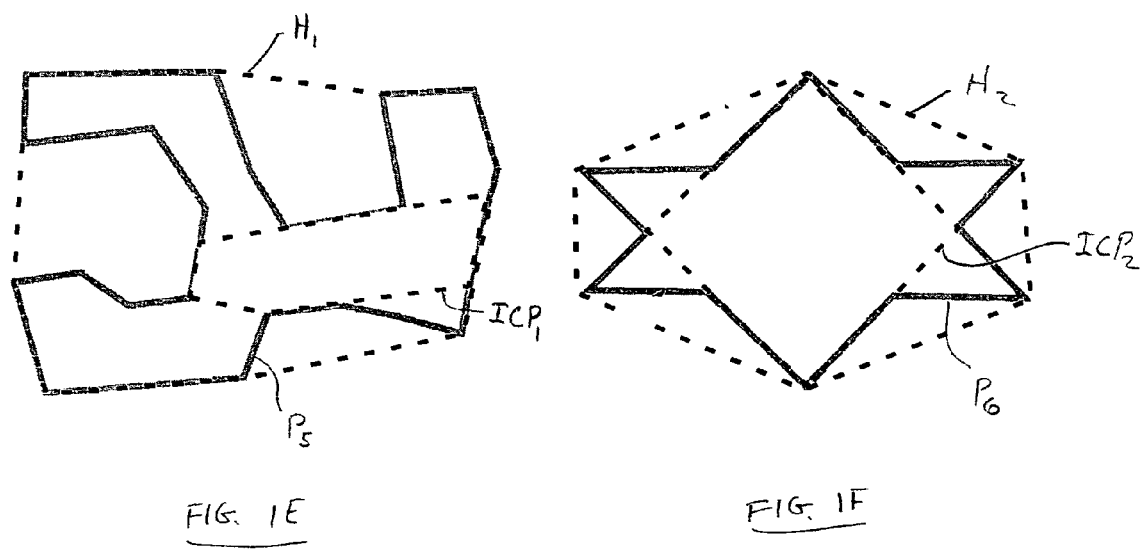
FIGS. 1E and 1F illustrate concave apertures.

According to the present subject matter, a one-dimensional channel (having an aperture with concave cross sectional geometry) can be described as having an aperture which features an inscribed convex polygon of a width smaller than the width of the object to be excluded and also a convex hull that has a diameter larger than the diameter of the object to be excluded. Inscribed means to construct a geometric shape inside another so they have points in common but the inscribed shape does not have any part of it outside the other. A convex hull is the smallest circumscribed convex shape that encloses an interior non-convex shape. Circumscribe means to construct a geometric shape outside another so they have points in common but the circumscribed shape does not have any part of it inside the other. FIGS. 1E and 1F illustrate exemplary concave apertures having perimeters $P_5$ and $P_6$, respectively, and inscribed polygons $ICP_1$, and $ICP_2$, respectively and convex hulls $H_1$ and $H_2$, respectively.

Figures 2A, 2B:
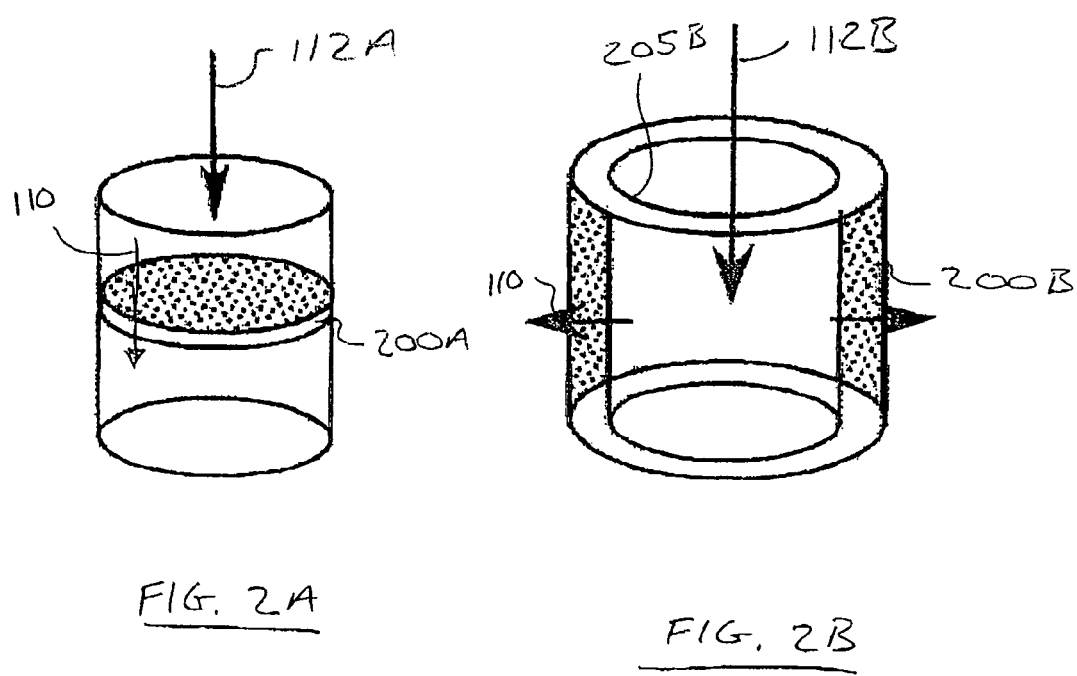
FIG. 2A illustrates a substrate having an axial flow configuration.
FIG. 2B illustrates a substrate having a radial flow configuration.

FIGS. 2A and 2B illustrate ways that a channel or an array of channel(s) can be configured in relation to a main flow direction. FIG. 2A illustrates substrate 200A configured for axial flow wherein the fluid flow enters in the direction denoted by arrow 112A and passes through the substrate in the direction denoted by arrow 110. The fluid flow, sometimes referred to as the filtrant, is substantially parallel to, or in the same direction as, the main fluid flow. In one example, substrate 200A includes a plurality of channels having one-dimensional geometry.

FIG. 2B illustrates substrate 200B configured for radial or lateral flow wherein the fluid flow enters along axis 112B and traverses the substrate in the direction aligned with arrow 110. Substrate 200B includes a plurality of one-dimensional channels. In a lateral flow configuration, as illustrated in the exemplary apparatus, the filtrant direction is substantially normal to the main flow. Lateral flow is sometimes referred to as cross flow.

The discussion regarding flow is merely exemplary. For instance, the fluid may be moved in a first direction to achieve a particular separation objective and later moved in a second direction to achieve a different objective. By way of example, the fluid flow may be reversed to dislodge the excluded objects from the channels or to isolate a particular object.

Figure 3A:
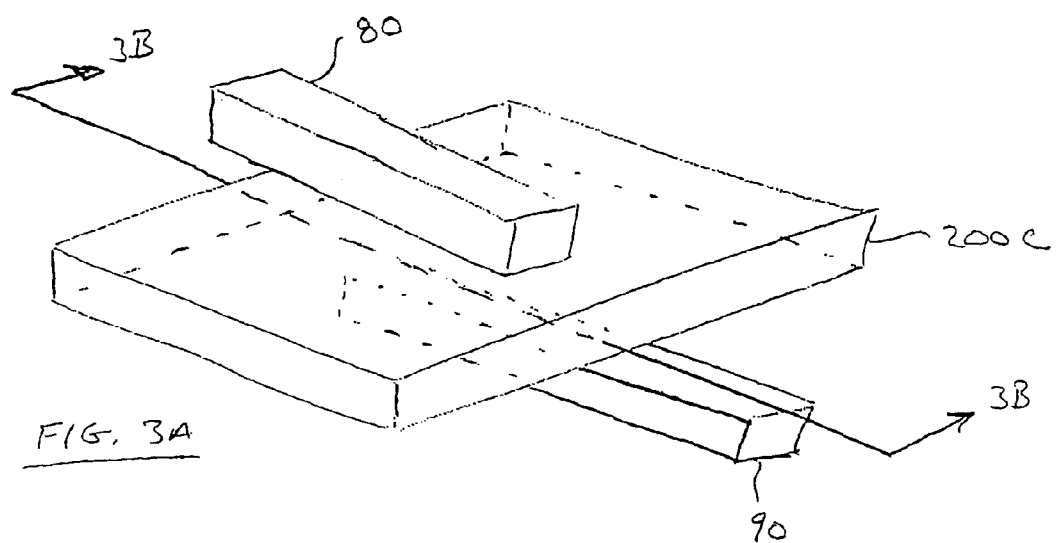
FIGS. 3A and 3B illustrate a substrate in the form of a membrane configured for axial flow.
Figure 3B:
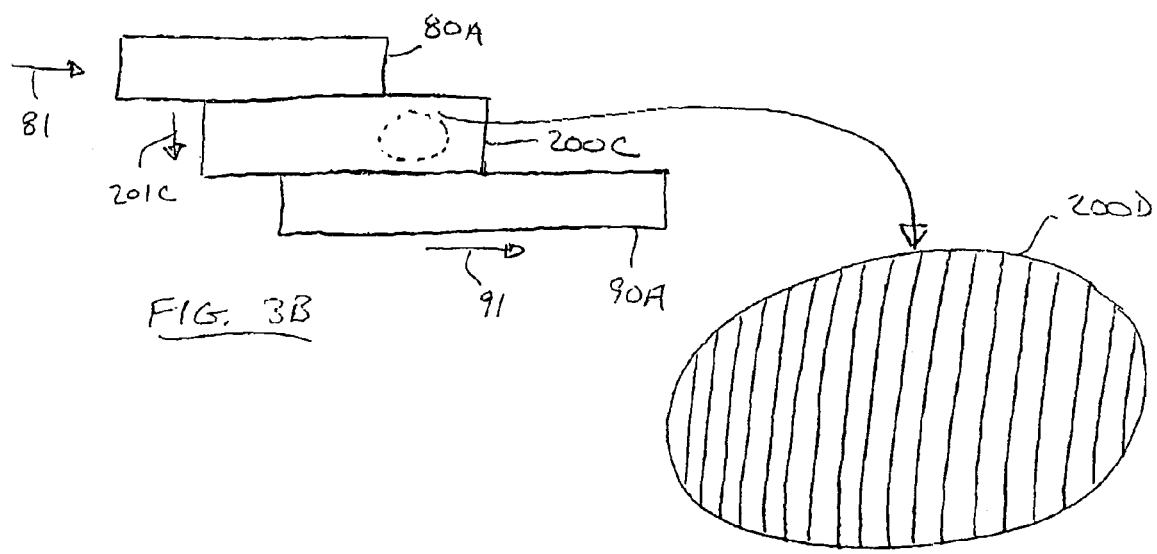

A one-dimensional channel or an array of one-dimensional channels may be employed within a subunit of a microfluidic device. FIGS. 3A and 3B illustrate an embodiment of one-dimensional channels (formed by sandwiching substrate 200C, which is fabricated with an array of one-dimensional channels as shown in 200D), between two substrates forming input conduit 80 and output conduit 90. Cut-away view 3B-3B is illustrated in FIG. 3B. Substrate 200C receives the filtrant via input conduit 80A and discharges the filtrate via output conduit 90A. Fluid flow in input conduit 80A is aligned with the direction of arrow 81, in substrate 200C aligned with the direction of arrow 201C and in output conduit 90A aligned with the direction of arrow 91. The structure of substrate 200C, when viewed with a side elevation, includes a plurality of channels, each of which is shown as a line in substrate 200D. The flow is in an axial configuration in the example illustrated; however the substrates and the embedded channels can be oriented for a lateral flow configuration. Various embodiments include an arbitrary number of input conduits and output conduits. In one example, a one-dimensional channel is fabricated directly in the top substrate or bottom substrate, thus eliminating the middle, or sandwiched, substrate.

FIGS. 4A-4G illustrate a variety of aperture cross section geometries, each of which has an elongate portion (many having a polygonal shape) which can be configured in size and shape to capture a target particle in one region and allow passage of fluid in another region. For example, FIG. 4A shows an aperture having a section of a ring or a semicircular arc wherein an elongate portion includes a curved section. As such, a target particle will be lodged between the two curved surfaces of the aperture and fluid can continue to pass near one or both ends of the arc. FIG. 4B illustrates a diamond shaped aperture wherein the diamond is elongate and has two acute interior angles and two obtuse angles. The narrow portion of the aperture (nearest the obtuse angles) will capture the target particle and fluid will flow in the region of the acute angles. FIG. 4C illustrates a triangular aperture having one obtuse angle and two acute angles. The narrow portion of the aperture (nearest the obtuse angle) will capture the target particle and fluid will flow in the region of the acute angles. FIGS. 4D-4G illustrate star-shaped and cross-shaped apertures, each of which can be viewed as having more than one elongate portion. FIGS. 4D, 4F and 4G can be viewed as combinations of triangle-shaped or diamond-shaped apertures and FIG. 4E can be viewed as a combination of rectangular-shaped openings.

In addition to those shown, other apertures are also contemplated including, for example, a combination of the illustrated shapes. For example, an aperture can include an oval or an elongate circular shape or a segment of a circle having a flat on a side (shaped like the letter D). Furthermore, a particular substrate can have apertures of more than one shape or more than one particular size.

FIGS. 5A-5D, as well as FIGS. 6A-6D, illustrate an exemplary procedure for micro fabricating one embodiment of a chip according to the present subject matter. FIGS. 5A-5D illustrate production of a molding master on a silicon wafer from which polydimethylsiloxane (PDMS) slabs incorporating an array of one-dimensional channels can be replicated. In FIG. 5A, a negative photoresist is spun onto a silicon wafer. The photoresist is baked and then partially exposed to ultraviolet light through a patterned photomask using a mask aligner as shown in FIGS. 5B-5C. The portion of the photoresist layer exposed to ultraviolet light is cross-linked by the radiation, and becomes insoluble in the developer solution. Exposing the photoresist layer to the developer solution, in FIG. 5D, removes uncross-linked photoresist and leaves raised structures of cross-linked photoresist on the surface of the silicon, essentially a negative relief image of the original photomask. The application of photoresist, ultraviolet light exposure, and development in developer solution may be repeated to create multi-level layered structures. Upon completion of the desired topography, the resulting master mold is passivated with fluorosilane to allow a PDMS slab be cast on the master mold and removed. In an alternative method, positive photoresist layers are used to create positive, relief images. In one method, microstructures are produced directly in silicon or other substrate materials by etching with reactive chemicals in gaseous or liquid phase, by ablating with focused laser beams, or by bombarding with directed charged particle beams such as ions, electrons or plasma.

FIGS. 6A-D illustrates the production of a PDMS microfluidics device using a master mold. The master mold is produced by photolithography and by additional surface modifications in FIGS. 6A-B. In FIG. 6C, liquid PDMS is poured onto the surface of the master mold and baked to cure the liquid PDMS into a soft, semi-solid slab. In FIG. 6D, the cured PDMS slab is peeled from the master mold, oxidized in an oxygen plasma, and then bonded against another piece of PDMS slab to form enclosed channels. In one method, the cured PDMS is peeled from the master mold and bonded to a substrate of material such as glass, quartz, or silicon. In one method, a curable thermoset or photocurable polymer, such as thermoset polyester, polycarbonate, or polymethylmethacrylate, is used in place of PDMS following a casting-replication process. In one method, the aforementioned microstructures are directly produced in a substrate by chemical etching, laser ablation, or charged particle bombardment and bonded to another substrate to form an enclosed fluidic channel.

Figure 7:
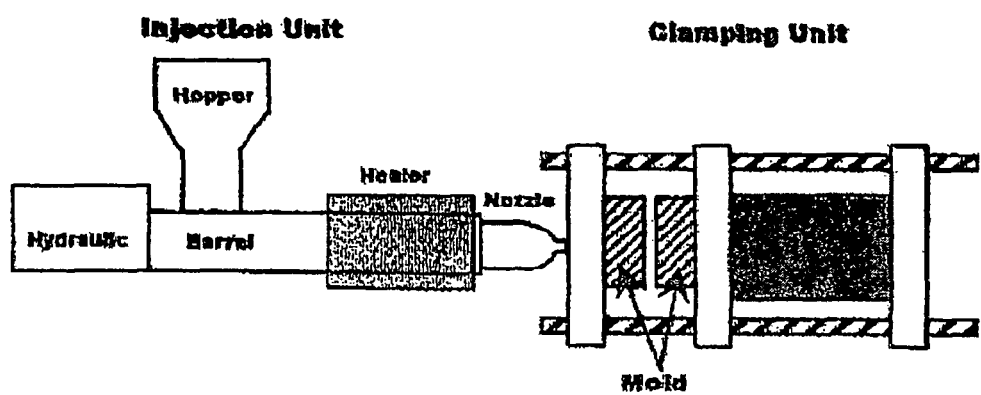
FIG. 7 illustrates an injection molding system for fabricating and replicating an exemplary device.

FIG. 7 illustrates an exemplary method to replicate microfluidic chips by injection-molding of thermoplastic materials. Solid plastic pellets are loaded into the hopper and softened under hydraulic pressure and temperature. The liquified material is then injected into a master mold with channel features. Upon cooling the plastic replica solidifies and is removed and bonded to another substrate to form an enclosed fluidic device.

Figure 8:
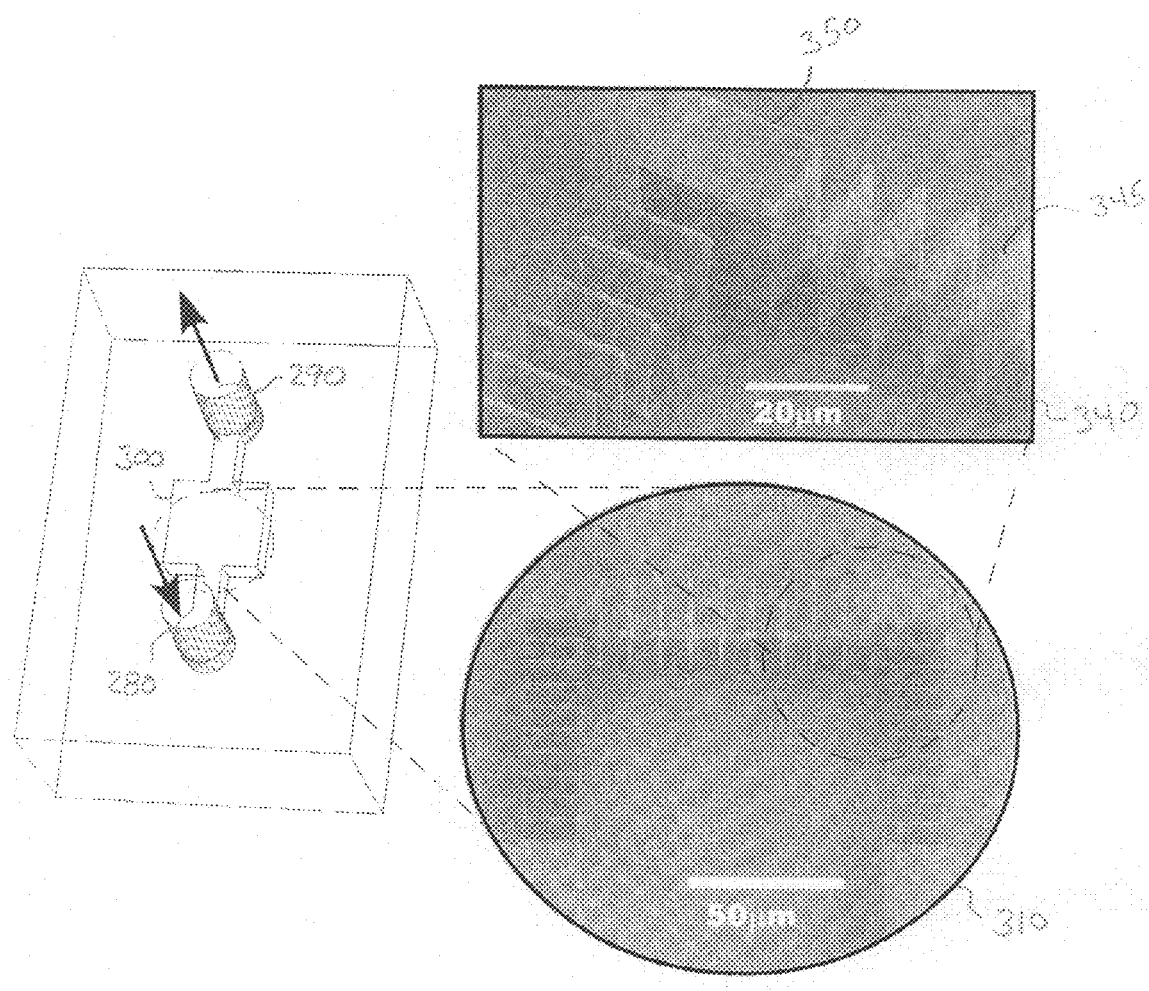
FIG. 8 illustrates scanning electron microscopy images of an exemplary device.

FIG. 8 illustrates scanning electron microscope images of exemplary device 300. Fluid flow is aligned with the direction illustrated by the arrows and enters at inlet 280 and exits at outlet 290. In particular, enlargement 310 and enlargement 340 each illustrate a plurality of thin channel walls 345 aligned in a pattern having "corner elements" 350. One-dimensional channels (3 μm aperture width by 20 μm aperture diameter by 20 μm channel axial length) are formed between thin channel walls 345 as well as between thin channel walls and corner elements 350. Analytes or biofluids are introduced into device 300 via inlet 280 by the hydrostatic pressure difference due to the difference in liquid height between inlet 280 and outlet 290. The channel surfaces may be modified chemically to enhance wetting or to assist in the adsorption of select cells, particles, or molecules.

Device 300 can be used to separate a subpopulation of cells from whole blood. Whole blood includes a complex mixture of white blood cells (leucocytes), red blood cells (erythrocytes), platelets, and plasma. Leucocytes are spherical-shaped with diameters ranging from 6 μm to 20 μm and are not easily deformed as they contain subcellular compartments such as nucleus and organelles. Erythrocytes, on the other hand, are disc-shaped fluidic sacs with nominal diameter of 7 μm and height of 2 μm. Because erythrocytes contain mostly fluids and have an extremely flexible cytoskeleton designed to support high degrees of deformation, they can be deformed easily and pass though constrictions even smaller than their smallest dimension. The use of one-dimensional channels provides mechanical exclusion to leucocytes in one dimension and leaves open areas or bypass regions next to the trapped or captured leucocytes such that the filtrate or carrier fluid can continue to flow. An erythrocyte can pass though a one-dimensional channel in a sideways mode.

Figure 9A:
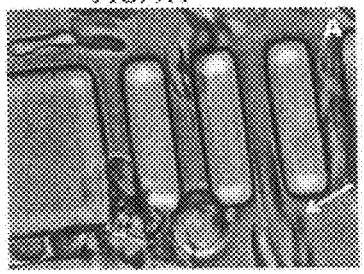
FIGS. 9A-9F illustrate the cell separation and enrichment operations of an exemplary device.
Figure 9B:
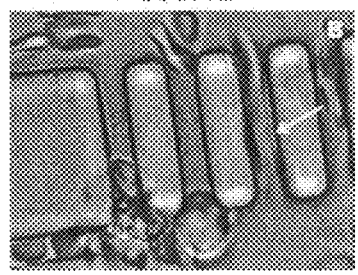
Figure 9C:
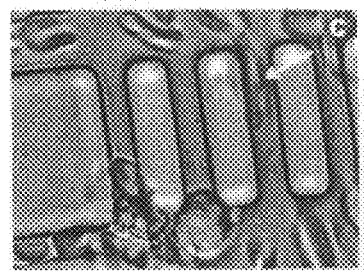
Figure 9D:
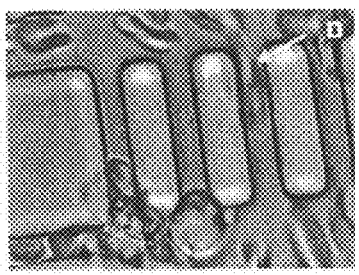
Figure 9E:
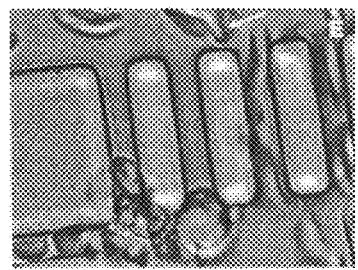
Figure 9F:
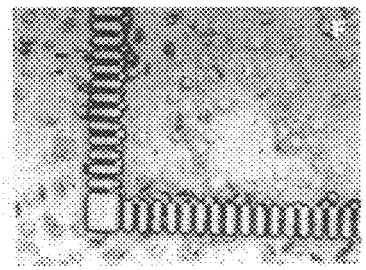

The following exemplary procedure can be used to separate leucocytes from whole blood using device 300. A 0.05 ml drop of human whole blood is added to approximately 0.2 ml isotonic phosphate-buffered saline (PBS) solution containing 1.5 mg/ml of $K_3$ EDTA as anticoagulant, 0.1 M of PBS, and 0.15 M of NaCl. Approximately 1 μL of this mixture is pipetted into the inlet reservoir of the device and additional buffer is added on top of the fluid reservoir to ensure steady gravity-driven flow. FIGS. 9A-9F show a sequence of photographs documenting the exclusion of leucocytes from whole blood mixture using device 300. As the mixture is passed through device 300, leucocytes (circular objects at the opening of each channel in the lower center and lower left corners of FIGS. 9A-9E) are unable to pass though the one-dimensional channels and accumulate near the channel entrances. However, since the aperture diameter is greater than the diameter of a leucocyte, the leucocytes do not block the flow completely and consequently the leukocytes remain undamaged and intact. Erythrocytes, however, are free to flip or deform while traversing through a one-dimensional channel. The white arrows in FIGS. 9A-9E indicate the trajectory of an erythrocyte moving through a one-dimensional channel by flipping onto its side. FIG. 9F shows a larger area of device 300 during the cell separation operation, where leucocytes (white circular objects) can be seen accumulating at more than 90% of channel entrances while erythrocytes passing freely through the channels. The inlet side of device 300 corresponds to the upper right corner of FIG. 9F.

Figures 10A, 10B, 10C, 10D, 10E, 10F, 10G, 10H:
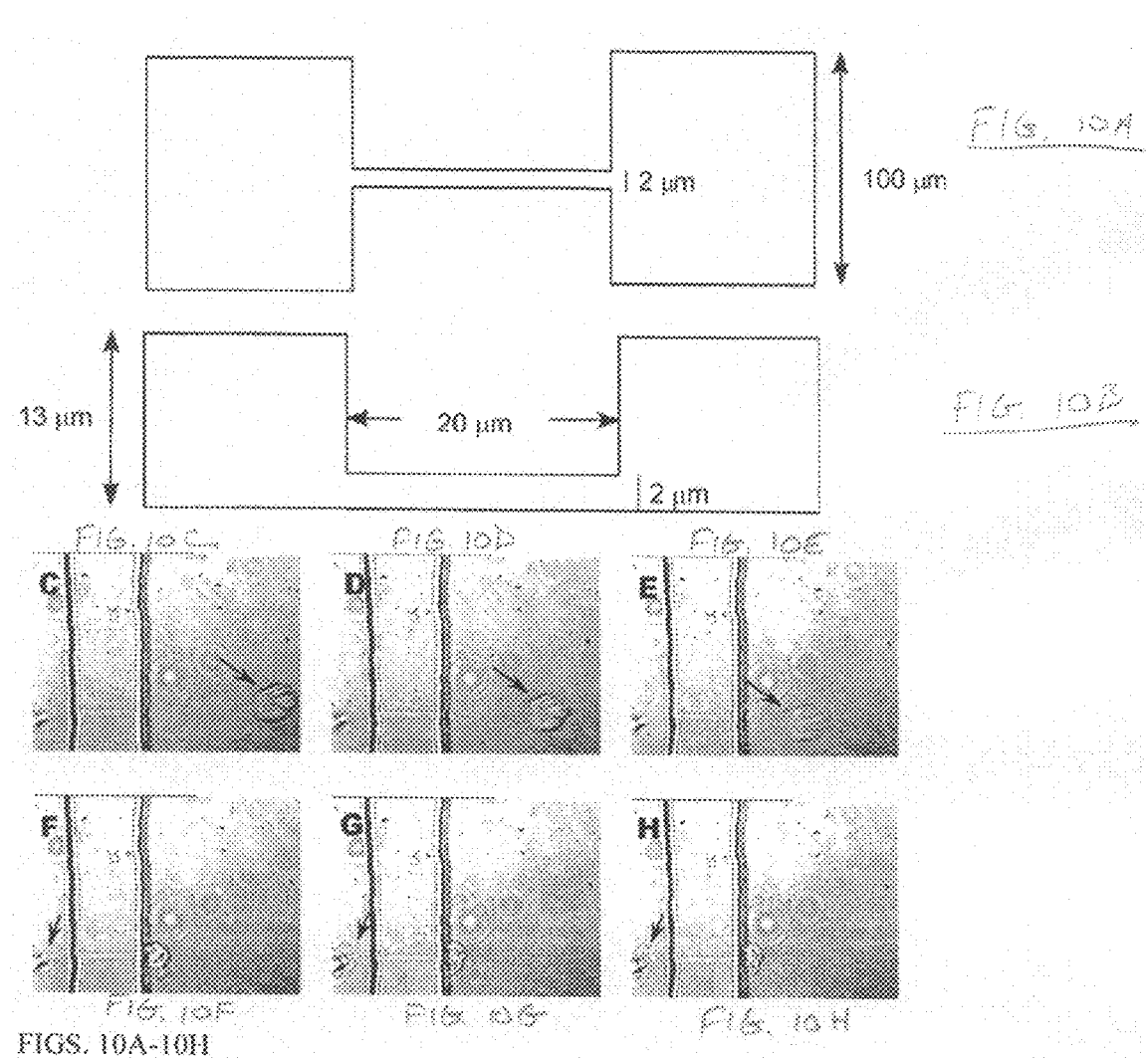
FIGS. 10A and 10B illustrate top and side elevation views of a zero-dimension channel.
FIGS. 10C-10H illustrate a cell lysing event by flowing a biofluid containing cells through a zero-dimensional channel.

A leucocyte-separation experiment can be conducted with a zero-dimensional channel, as illustrated in FIG. 10, for purposes of comparison. FIGS. 10A and 10B show the top and side elevation views of a channel having a square cross section of 2 μm by 2 μm and an axial length of 20 μm coupled to input and output chambers, each having dimensions of 100 μm by 13 μm. Identical preparation method is used to prepare the blood mixture and a syringe is used to deliver the mixture into the inlet chamber. FIGS. 10C-10H show a sequence of images of a leucocyte (marked by arrows) approaching the channel and completely blocking the channel, and having partially expelled its contents under the applied pressure. A leucocyte blocking the zero-dimensional constriction forms a complete blockage and the separation function ceases once the fluid flow is precluded.

A theory as to the physics of channel blockage in relations to the local pressure experienced by cells is illustrated in FIGS. 11A-11C, 12, 13, 14A, 14B, 15A and 15B. FIGS. 11A-11C illustrates various scenarios that can affect the local pressure experienced by a biological cell in separation processes. FIG. 11A illustrates the hydrodynamic pressure imparted by a carrier fluid as it flows past a cell. FIG. 11B illustrates the pressure experienced by a cell completely clogging a single channel. FIG. 11C illustrates the pressure experienced by a cell clogging a channel in the presence of multiple parallel channels available for flow bypass. As discussed herein, a one-dimensional channel provides improved performance relative to that of a zero-dimensional channel in terms of reducing cell lysing since a one-dimensional channel permits the carrier fluid to flow past the trapped cells and reduce the pressure escalation associated with the complete blockage of a zero-dimensional channel.

Figure 12:
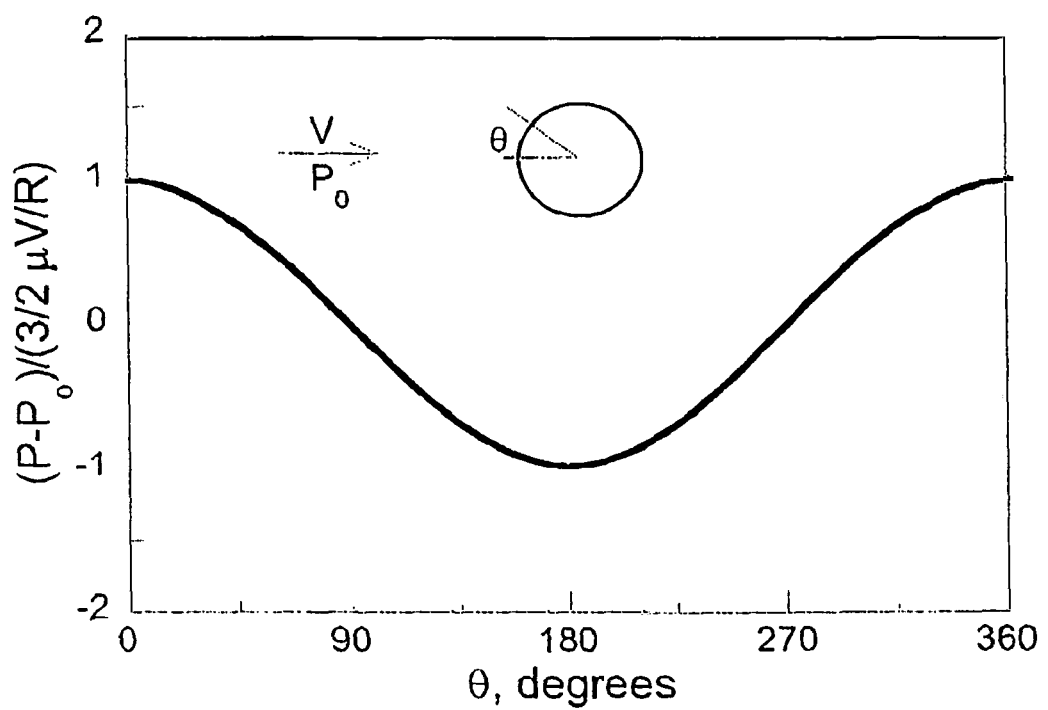
FIG. 12 illustrates the pressure distribution around a free spherical particle in a flow.

FIG. 11A illustrates pressure encountered by a single cell in flow. The pressure experienced by a cell in a separation environment depends strongly on whether the carrier fluid is able to pass around the cell. When a cell is excluded by a one-dimensional channel, the fluid is still able to flow around the cell, and thus the pressure is essentially the same as if the cell is a free particle in the flow. The upstream half of the cell experiences a higher pressure from the direct impingement of fluid, which leads to a local distribution of pressure around the cell (P) given by:

$$P = P_0 + \frac{3}{2}\frac{\mu V}{R}\cos\theta \qquad \text{Eq. (1)}$$

where $P_0$ is the upstream pressure (for convenience, the downstream pressure is assumed to be 0), μ is the viscosity of the carrier fluid, R is the radius of the cell, and V is the velocity of the fluid. The angular distribution of the pressure from Eq. (1) is plotted in FIG. 12. FIG. 12 shows pressure distribution from a flow around a spherical object where zero degree is defined as the angle opposite of the upstream flow direction.

The maximum pressure difference ($\Delta P_{max}$) between 0° (fluid impinging) and 180° (wake) is given by:

$$\Delta P_{max} = 3\frac{\mu V}{R} \qquad \text{Eq. (2)}$$

Figure 13:
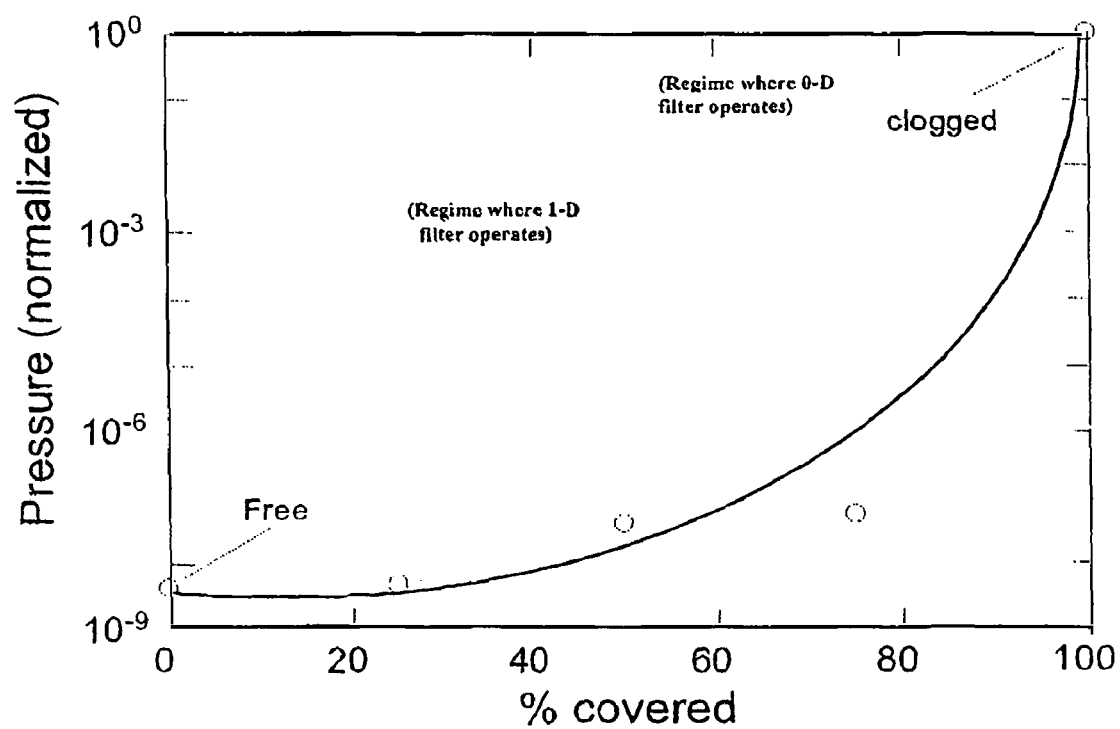
FIG. 13 illustrates the pressure experienced by a cell lodged at a separation channel entrance as a function of the percentage of channel cross-sectional area blocked.

FIG. 11B illustrates a cell clogging a single channel. In the case where the cell completely clogs a zero-dimensional channel (or pore), the carrier fluid is unable to recombine behind the cell and the pressure across the cell is simply the same as the externally applied pressure differential (i.e. the syringe pump pressure.) The externally applied pressure differential is always larger than the pressure difference from the flow around a cell (e.g. when a cell is trapped by a one-dimensional channel), sometimes by several orders of magnitude, because the former is what is required to drive the flow through the entire filter and the latter is only a small pressure drop from the fluid wrapping around a cell. For a partially clogged channel, some fluid is allowed to pass by the cell and relieve the pressure difference across the cell. The degree of relief is related to the unobstructed cross-sectional area available for flow. FIG. 13 shows the effect on the cell pressure as a cell covers the channel opening. In other words, FIG. 13 illustrates cell pressure as a function of the percent of channel area blocked. Data points were obtained by solving the Navier-Stokes equation numerically for a 5 μm (diameter) by 10 μm (axial length) cylindrical channel partially blocked by a 5 μm (diameter) cell.

FIG. 11C illustrates clogging of one channel in an array of multiple parallel channels. In cases where systems of unclogged parallel channels are available to allow the carrier fluid to bypass and recombine at the exit side of the filtration area, the pressure experienced by the clogged cell is equivalent to the pressure drop across the unclogged parallel channels. For one unclogged parallel channel, the pressure drop from viscous dissipation ($\Delta P_{channel}$) is given by the Poiseuille equation:

$$\Delta P_{channel} = \frac{32\mu VL}{D^2} \qquad \text{Eq. (3)}$$

where μ is the viscosity of the carrier fluid, D is the diameter of the channel, L is the axial length of the channel, and V is the velocity of the fluid.

For n parallel channels, the pressure drop is reduced by a factor n, since more cross-sectional area is available for flow:

$$\Delta P_{n-channel} = \frac{32\mu VL}{nD^2} \qquad \text{Eq. (4)}$$

A comparison of this pressure drop to the pressure of a trapped cell in a one-dimensional channel (Eq. (2)) can be made by making simplifying assumptions. Assume that the axial length of the pore is at least five times the pore diameter (L=5D) and that the diameter is twice the radius of the channel (D=2R) in Eq. (4). Accordingly, the results are given by:

$$\Delta P_{n-channel} = \frac{32\mu V(5(2R))}{n(2R)^2} = \frac{80}{n}\frac{\mu V}{R}. \qquad \text{Eq. (5)}$$

A comparison of Eq. (5) with Eq. (2) reveals that n, the number of unclogged bypass channels, should be approximately 80/3 or 27 in order to relieve the pressure of one clogged channel to the point of equivalent to cell trapping by a one-dimensional channel. In other words, if more than 4% of the total channels are clogged in a substrate consisting of purely zero-dimensional channels, then the remaining unclogged channels become less effective than a single one-dimensional channel in terms of circumventing the pressure build-up. This poses a capacity issue when devices based on zero-dimensional channels are used to isolate cells.

Thus, an increased probability of cell lysing arises from having a multitude of zero-dimensional channels. The pressure experienced by the cell is directly related to the tension on the cellular membrane. In other words, the pressure differential forces the cell to stretch, and when the increase in surface area exceeds 2-4% of the original surface area, the cell is lysed.

Figures 14A, 14B:
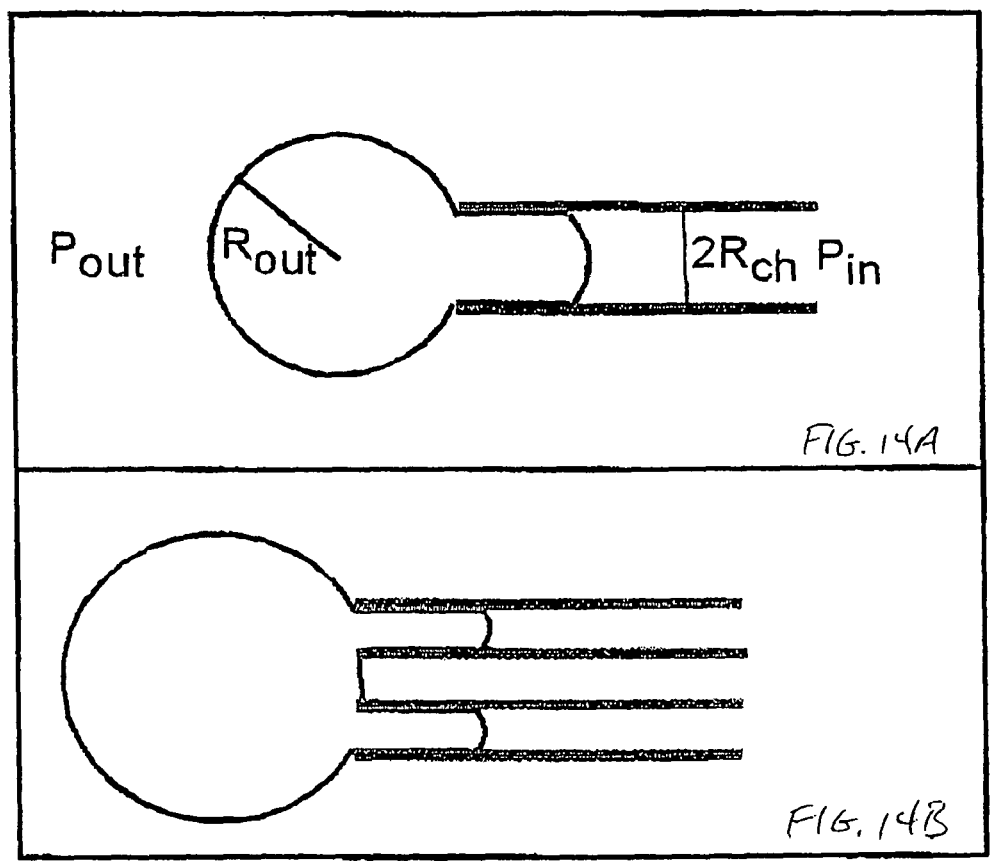
FIG. 14A illustrates cellular membrane deformation as a result of a cell lodged at a pore subject to applied pressure differential.
FIG. 14B illustrates cellular membrane deformation as a result of a cell lodged at two pores subject to applied pressure differential.

FIG. 14A illustrates a channel of diameter $2R_{ch}$ completely clogged by a cell with the external diameter $R_{out}$. In the simplified geometry shown in FIG. 14A, the pressure required to sustain curvature to the membrane tension is by Laplace's law:

$$\Delta P = 2\tau\left(\frac{1}{R_{ch}} - \frac{1}{R_{out}}\right) \quad \text{Eq. (6)}$$

where $\Delta P$ is the pressure difference between the outside ($P_{out}$) and the inside ($P_{in}$) of the channel, $R_{ch}$ is the radius of curvature inside the channel, $R_{out}$ is the radius of curvature of the remaining cell volume outside of the channel, and $\tau$, the membrane tension, is proportional to the surface area change.

FIG. 14B illustrates two channels simultaneously clogged by a cell. In such a case, where a cell covers two pores simultaneously, the membrane tension is given by adding up the curvatures:

$$\Delta P_{2-pores} = 2\tau\left(\frac{1}{2R_{ch}} - \frac{1}{R_{out}}\right) \quad \text{Eq. (7)}$$

Figures 15A, 15B:
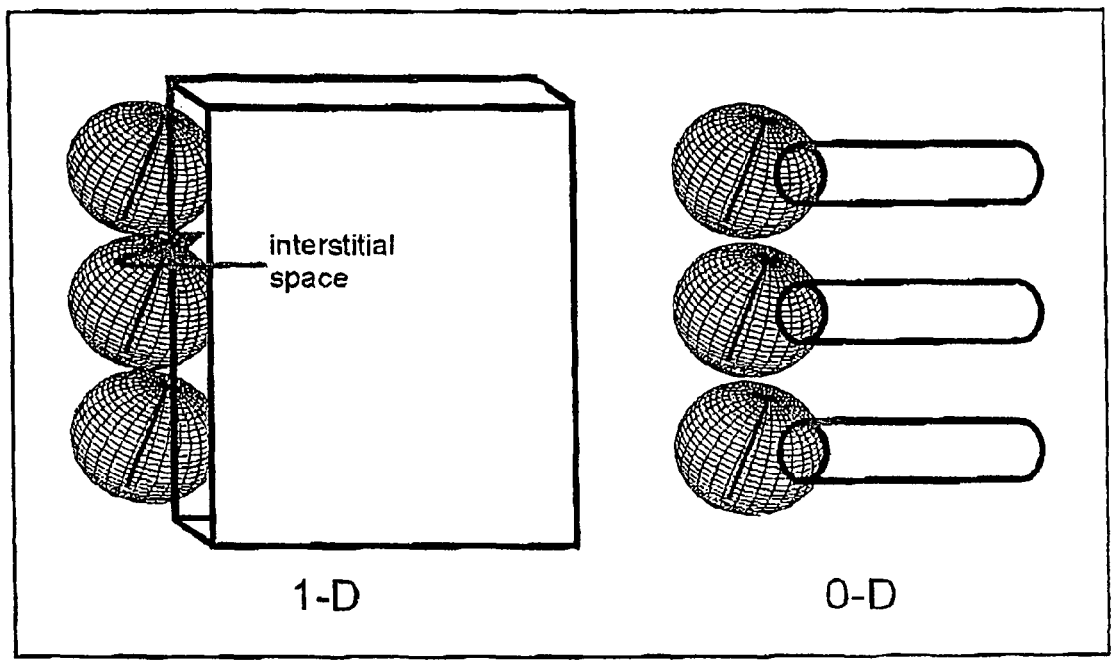
FIGS. 15A and 15B illustrate modeled views of channels with target particles.

From Eq. (7), it will be noted that for a constant pressure differential, if a cell covers more zero-dimensional channels (pores), the membrane tension $\tau$ will increase, and the probability of cell lysing increases. A difference between a one-dimensional channel and multiple closely packed zero-dimensional channels (pores, as analyzed above), includes the ability of one-dimensional channels to allow flow to pass around a cell in the same channel, keeping the pressure drop across the cell small, and thus minimizing damage to the trapped cell. In situations where a one-dimensional channel trap cells in high density, interstitial spaces between closely-packed cells are available for fluid flow, as illustrated in FIG. 15A. The zero-dimensional channels illustrated in FIG. 15B do not provide an interstitial space.

Separation, isolation, and enrichment of subpopulations of biological cells from a complex biofluid mixture may have clinical applications in disease diagnosis. The present subject matter can be used to detect alterations in cell populations as well as the presence of parasites or foreign matters in biofluids to facilitate diagnosis.

In one embodiment, an array of one-dimensional channels can be integrated into a diagnostic device to facilitate the collection and enrichment of leucocytes and malaria-infected erythrocytes in the diagnosis of malaria. Severe malaria is caused by the parasite *Plasmodium falciparum*. The parasite invades the erythrocytes in blood, and its maturation process causes the erythrocytes to lose deformability. The physical changes of invaded erythrocytes at the cellular level include the incorporation of knob-associated histidine-rich protein (KAHRP) in the cellular membrane, increased internal viscosity due to the parasite presence, and a more spherical surface-to-volume ratio. Microfluidic observations have provided visual confirmation that parasitized erythrocytes frequently result in capillary blockage, which has been proposed as the underlying pathogenesis mechanism.

Current diagnostic protocol for malaria diagnosis includes microscopic examination of blood smear and the visual identification of malarial parasites. Two microscopy procedures are recommended by the Center for Disease Control (CDC) and the World Health Organization (WHO): in thick smear preparation, erythrocytes are lysed, and a microscopist visually counts the number of parasites against the leucocytes present in 100 fields under 100× oil-immersion objective and converts the ratio accordingly; in thin smear preparation, erythrocytes are not lysed, and a microscopist examines 300 fields under the same magnification and counts the parasitized erythrocytes among normal erythrocytes.

The present subject matter can be applied to the field of malaria diagnostics. The apparatus can selectively isolate leucocytes as well as parasitized erythrocytes while allowing normal erythrocytes to pass though. The present subject matter also acts as a cell concentrator as the isolated cells accumulate in an enclosed volume, thus reducing the number of fields necessary to achieve the same cell counts compared to the thick smear protocol. In addition, one example of the present subject matter provides a reduced pressure drop across the substrate.

FIGS. 16A-16F illustrate a sequence of photographs showing trapping of malaria-infected red blood cells (RBC) and white blood cells (WBC) while allowing the passage of uninfected red blood cells using an exemplary device. One microliter of sample analyte, including malaria-infected human blood diluted with RPMI growth media to ~10,000 cells/μL is pipetted into the inlet. Additional growth media and dyes may be added to control the flow rate and improve the visualization of cells and parasites. In one example, the channel surfaces are modified chemically to improve trapping of desired cells. The exemplary device is then placed onto a Nikon TE300 inverted microscope and inspected under a 100× oil-immersion objective magnification. FIG. 16A shows three parallel one-dimensional channels of aperture dimensions 4 μm width by 16 μm diameter (channel height) and an axial length of 20 μm, formed between four rectangular walls. The fluid flow is from right to left and driven by the hydrostatic height difference between the inlet and outlet reservoirs (gravity-driven). Immediately adjacent to the channel entrances are one trapped leucocyte (white blood cell) and four infected erythrocytes (RBC). The malaria-infected erythrocytes are spherical and are unable to pass through the one-dimensional channels. Young *P. falciparum* parasites corresponding to the developmental stage of ring-stage trophozoite are visible in the form of a small white granule inside two of the infected erythrocytes. FIGS. 16A-16F show the unrestricted movement of an uninfected erythocyte (marked by black arrow) through a one-dimensional channel by flipping onto its side. Thus the entrance side of the one-dimensional channels becomes enriched with leucocytes and infected erythrocytes. These cells may be enumerated to document the parasite concentration and the developmental stages of the parasites may be accurately identified.

In addition to malaria, the present subject matter can be used for monitoring of CD4+ T-lymphocytes (CD4+ T-cells) in Human Immunodeficiency Virus (HIV) diagnostic and monitoring. The absolute CD4+ T-lymphocyte count can serve as a criterion to initiate antiretroviral therapy and opportunistic infection prophylaxis in HIV-infected patients. The reduction of CD4+ T-lymphocytes, which is a subpopulation of leucocytes (white blood cells), strongly correlates to the decline of the immunological defense. Monitoring of CD4+ T-lymphocytes (CD4+ T-cells) level every 3-6 months in all HIV-infected persons has been recommended by the CDC Public Health Service as a way to initiate appropriate treatment strategies and to evaluate treatment efficacy.

In some laboratories, the absolute CD4+ T-cell number is established using the product of three laboratory techniques: the total white blood cell count, the percentage of white blood cells that are lymphocytes, and the percentage of lymphocytes that are CD4+ T-cells. Single platform flow cytometers such as FACSCount (BD Biosciences) is commercially unavailable in some developing countries or as a portable device.

Low cost alternatives for CD4+ T cell monitoring include nonflow bead-based labeling methods with minimal microscope requirements such as magnetic Dynabeads (DynalBiotech ASA) and latex cytospheres (Beckman Coulter). Although the measurements from these methods in general correlated well with that from flow cytometry under experienced hands, due to increased manual handling and reading assay, inconsistent results can incur, as exemplified by a recent report that number of positive cell can depend on how vigorous the samples were shaken during reagent mixing.

The present subject matter can be used to remove erythrocytes and accumulate leucocytes prior to appropriate immunophenotyping to distinguish CD4+ T-lymphocytes from other leucocytes. Lymphocytes can be distinguished from other leucocytes (e.g. monocytes and granulocytes) on the basis of size, granularity, or morphology and the absolute distinction of CD4+ T-cell within lymphocytes can be accomplished via immunophenotyping. In manual counting methods such as aforementioned Dynabeads and Cytospheres, erythrocytes must be lysed with appropriate reagents so leucocytes can be clearly seen, since the ratio of leucocyte to erythrocyte in whole blood is 1:1000. Employing chemical lysing reagents, however, has been known to reduce CD4+ T cell counts by as much as 10% when compared to no-lyse methods because lysing agents can lead to destruction of the cell membrane as well as the epitopes for fluorescence labeling. This type of cell count reduction occurs nonuniformly among subclasses of leucocytes. In HIV monitoring, where falling T-cell count signals the progression of the disease, such erroneous reduction in absolute count can misguide the physicians in interpreting the progress of treatment.

In addition to the foregoing disease diagnostic applications, cancer-related rare cells can also be detected using the present subject matter. Tumor cells can exfoliate from solid tumors and transport throughout the body via the blood stream. These circulating tumor cells (CTCs) are present in extremely low concentration in the peripheral blood, estimated to be on the order of one tumor cell per $10^6$ to $10^7$ mononuclear cells, which is equivalent to one tumor cell per 0.5 ml to 5 ml of peripheral blood. At such low concentration, a sample with estimated 100 million cells must be screened in order to detect at least one CTC with 99.995% certainty. An automatic digital microscopy (ADM) scanning at a typical speed of 800 cells/second would require 18 hours to complete a sample that size, and even with an improved optical system, it is estimated that the scanning task would still require about one hour with additional manual examination.

The CTCs can be distinguished from normal cells by two physical characteristics: (1) tumor cells preferentially express cytokeratins as integral components of cytoskeletons, and as such may be distinguished by means of specific antibodies, and (2) most CTCs have whole cell areas 2.8 to 5.7 times larger than normal leucocytes. Current enrichment methods of CTCs can be divided into immunological-based approach (e.g. positive and negative immunomagnetic separation) and physical separation method (based on filtration using a polycarbonate filter with 8-μm pores). Using filtration, researchers have compared CTCs in patients with hepatocellular carcinoma before and during surgery, detected CTCs in peripheral blood of breast cancer patients and correlated to the disease stage, and found that spontaneous circulation of CTCs in peripheral blood is a sign of tumor progression and tumor spread in primary liver cancer patients, all with high sensitivity.

Since the size difference between cancerous cells and normal cells is considerable, the present subject matter can be used to isolate the circulating tumor cells from whole peripheral blood or spinal fluids and the system may be configured for inspection under a microscope without disassembling the filtration housing, and without concern of lysing the rare cancerous cells.

Figure 17:
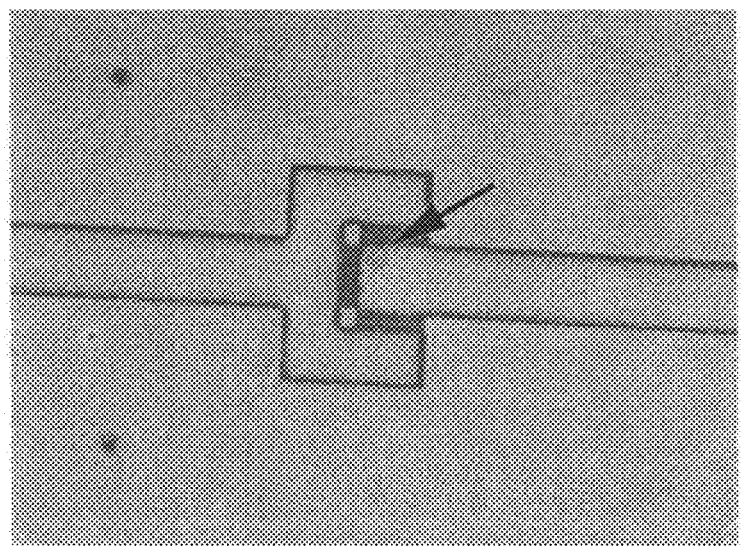
FIG. 17 illustrates trapping of a cancer cell by an exemplary device.

FIG. 17 includes a photograph of a colon-rectal cancer cell (HT-29 cell line) isolated using the present subject matter. The flow direction in FIG. 17 is from right to left, and the biofluid consists of a dilute mixture of HT-29 cancer cells in McCoy's cell growth medium. The arrow in FIG. 17 marks the trapped cancer cell. Furthermore, additional devices or methods for cell separation (e.g. dielectrophoresis, electrophoresis, electrokinetic based separation, magnetically based separation, optically based cell sorting) or cell screening (e.g. fluorescence-based screening to identify cancer cells tagged with a dye-labeled antibody to cytokeratin from other cells) can be integrated downstream of this device to confirm the identity of the isolated cancerous cells.

Additional applications involving separation, concentration and isolation addressed by the present subject matter include fetal cell monitoring in maternal blood for prenatal diagnostic of genetic disorders and prion detection. A prion includes a small infectious proteinaceous particle which resists inactivation by procedures that modify nucleic acids. In addition, the present subject matter can be used with fetal cells (fetal cells are larger than maternal cells) and other micro-biological particulates or nano-biological particulates.

As used herein, filtration includes collecting the clarified filtrate as well as isolating and concentrating solids. Examples of filtering include partitioning biological cells and micro-particulates or nano-particulates. Examples of the present subject matter can be used for filtering, separating, isolating, concentrating and purifying.

In one example, the present subject matter includes a substrate material including, but not limited to, polymeric materials (polydimethylsiloxane (PDMS), polymethylmethacrylate (PMMA), polyethylene, polyester (PET), polytetrafluoroethylene (PTFE), polycarbonate, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In addition, the substrate can be fabricated of porous membranes, woven or non-woven fibers (such as cloth or mesh) of wool, metal (e.g. stainless steel or Monel), glass, paper, or synthetic (e.g. nylon, polypropylene, and various polyesters), sintered stainless steel and other metals, and porous inorganic materials such as alumna, silica or carbon.

The flow can be delivered by, for example, methods and devices that induce hydrodynamic fluidic pressure, which includes but is not limited to those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion); surface-wetting principles (e.g. electrowetting, chemically, thermally, and radioactively induced surface-tension gradient).

In addition, fluid drive force can be provided by gravity feed, surface tension (like capillary action), electrostatic forces (electroosmotic flow), centrifugal flow (substrate disposed on a compact disc and rotated), magnetic forces (oscillating ions causes flow), magnetohydrodynamic forces and a vacuum or pressure differential.

Fluid flow control devices, such as those enumerated with regard to methods and devices for inducing hydrodynamic fluid pressure or fluid drive force, can be coupled to an input port or an output port of the present subject matter. In one example, multiple ports are provided at either or both of the inlet and outlet and one or more ports are coupled to a fluid flow control device.

The present subject matter can be fabricated by replication or direct fabrication. Examples include semiconductor fabrication techniques and methods including photolithography, growing a crystalline structure, and etching (reactive ion etching and wet etching), laser ablation, replica molding, injection molding and embossing (application of heat and pressure) and imprinting.

In various examples, the present subject matter is fabricated in the form of a membrane. The membrane can have a uniform thickness or a predetermined thickness gradient. In addition, the uniformity and numerosity of the pores can be tailored for a particular application. Furthermore, one or more particular coatings can be applied to an external or internal surface of the substrate. For example, the channel surfaces may be modified chemically to increase or decrease the surface interaction with the object or particulate to enhance device performance.

The present subject matter can be integrally fabricated on a chip or constructed off chip and then assembled onto a chip.

A micro-fabricated or nano-fabricated device and method of the present subject matter can be used to separate or filter microscopic or nanoscopic biological objects, such as biological cells, macromolecules, colloidal particles, particulates, or micro-beads.

A plurality of one-dimensional channels can be configured such that the longitudinal axis of each channel is aligned in parallel for axial flow. A radial configuration of longitudinal axis (converging at a point) yields a cross-flow filter. Other configurations are also contemplated, including, for example, a random arrangement of axes.

According to one example, an apparatus has one or more channels having an aperture cross sectional geometry such that a chord of length larger than the diameter of the object to be excluded can be drawn.

In particular, a channel having a convex cross sectional aperture, according to one example of the present subject matter, has an aperture width less than the width of the object to be excluded and the aperture diameter is greater than the diameter of the object and also greater than the aperture width.

In addition, a channel having a concave cross sectional aperture, according to one example of the present subject matter, has an inscribed convex polygon of a width and a diameter less than the width of the object to be excluded and a convex hull that has a diameter greater than the diameter of the object to be excluded.

In one example, the object is allowed to move in a direction parallel to the fluid flow. In other examples, the object is allowed to move in a direction at a particular angle relative to the fluid flow. That angle can be normal or at any other angle. For example, the object may be drawn by capillary action or diffusion in a direction that is not aligned with the fluid flow direction.

Conclusion

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A microfluidic device for separating a biological object from a fluid, the device comprising:
    an input port; and
    a microfabricated substrate in fluidic communication with the input port, the microfabricated substrate comprising an inlet channel in fluidic communication with a plurality of channels, wherein at least one channel of the plurality of channels includes an aperture configured to exclude an object from a fluid while allowing passage of the fluid through the at least one channel,
    wherein the aperture is configured such that the object covers about 75% or less of a cross-sectional area of the aperture,
    wherein the configuration of the aperture reduces the fluid pressure applied to the object,
    wherein the microfabricated substrate is sealed to a substrate that is capable of transmitting light and forms a surface of the inlet channel and the at least one channel, and
    wherein the longitudinal axis of the at least one channel of the plurality of channels is oriented in a different direction than a main axis of flow in the inlet channel.

2. The device of claim 1 wherein some of the channels in the plurality of channels are oriented for axial flow of the fluid.

3. The device of claim 1 wherein the plurality of channels is oriented for radial flow of the fluid.

4. The device of claim 1 wherein the object includes at least one of a biological particle.

5. The device of claim 1 wherein the aperture is configured to exclude a leucocyte.

6. The device of claim 1 wherein the aperture is configured to exclude a tumor cell.

7. The device of claim 1 wherein the aperture is configured to exclude an infected erythrocyte.

8. The device of claim 1 wherein the plurality of channels includes at least one of a polycarbonate, silicon, fused silica, ceramic, glass, thermoset polyester, and a cross-linked polymer.

9. The device of claim 1 wherein the plurality of channels includes a cross-linked polymer; and
wherein the cross-linked polymer includes at least one of polydimethylsiloxane (PDMS), polymethylmethacrylate (PMMA), polyethylene, polyester (PET), polytetrafluoroethylene (PTFE), polycarbonate, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide and polyimide.

10. The device of claim 1 further including a fluid flow control device coupled to a port.

11. The device of claim 10 wherein the fluid flow control device is configured to apply at least one of a pressure differential, a gravitational force, a surface tension force, an electrostatic force, an electrokinetic force, an electroosmotic force, a centrifugal force, a magnetic force and a vacuum.

12. The device of claim 1 wherein a size of the object is approximately that of at least one of a cancer cell, a malaria infected cell, an HIV infected cell, a lymphocyte, a prion particle, a prion-infected cell and a fetal cell.

13. The device of claim 1 configured for detecting a blood-borne disease.

14. The device of claim 1 configured for enumerating leucocytes in blood.

15. The device of claim 1 configured for detecting malarial parasites in blood.

16. The device of claim 1 configured for enumerating cancer cells in a body fluid.

17. The device of claim 1 configured for detecting a parasite-infected erythrocyte in blood.

18. The device of claim 1 configured for detecting HIV infection.

* * * * *